United States Patent [19]

Mack

[11] Patent Number: Plant 5,327

[45] Date of Patent: Nov. 6, 1984

[54] CHRYSANTHEMUM PLANT NAMED TOTEM

[76] Inventor: Grace H. Mack, 108 Wahackme Rd., New Canaan, Conn. 06840

[21] Appl. No.: 435,693

[22] Filed: Oct. 21, 1982

[51] Int. Cl.[3] ..... A01H 5/00

[52] U.S. Cl. ..... Plt./79

[58] Field of Search ..... Plt./79

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum cultivar named Totem having flat capitulum form, decorative capitulum type, orange bronze ray floret color, diameter across face of capitulum up to 60 mm., medium plant height, spreading branching pattern, average natural season flowering date of Sept. 20, and average flowering response period of seven (7) weeks in photoperiodic controlled short day programs.

3 Drawing Figures

The present invention comprises a new and distinct cultivar of *Chrysanthemum morifolium*, Ramat., hereinafter referred to by the cultivar name Totem.

Totem is a product of a planned breeding program which had the objective of creating cultivars with decorative capitulum type, medium height, spreading branching pattern, durable inflorescence, seven (7) week flowering response period, and orange bronze ray floret color under outdoor natural season conditions.

Totem was originated from a cross made by Grace H. Mack in a controlled breeding program in New Canaan, Conn. in the year 1966. The male parent was Y3363, an orange decorative, an undisseminated seedling selected by the originator from a cross between Minnautumn and M150. The female parent was 539, a bronze decorative, an undisseminated seedling selected by the originator from a cross of two unnamed seedlings (Y2392×M226).

Totem was discovered and selected as a flowering plant within the progeny of the stated cross by Grace H. Mack in September of 1967 in her outdoor garden in New Canaan, Conn. The first act of asexual reproduction of Totem was accomplished when vegetative cuttings were taken from the initial selection in 1968 in New Canaan, Conn. by Grace H. Mack. Horticultural examination of selected units initiated June 1979 has demonstrated that the combination of characteristics as herein disclosed for Totem are firmly fixed and are retained through successive generations of asexual reproduction.

Totem has not been observed under all possible environmental conditions. The phenotype may vary significantly with variations in environment such as temperature, light intensity, and day length. The following observations, measurements, and comparisons describe plants grown in a field in Salinas, Calif. Rooted cuttings were established in soil in one gallon containers maintained outdoors under the natural temperature and day length prevailing during July through September. Single pinching was practiced with all branches and buds retained.

The following traits have been repeatedly observed and are determined to be basic characteristics of Totem which in combination distinguish this chrysanthemum as a new and distinct cultivar;

(1) Flat capitulum form.

(2) Decorative capitulum type.

(3) Orange bronze ray floret color.

(4) Diameter across face of capitulum up to 60 mm.

(5) Medium plant height.

(6) Spreading branching pattern.

(7) Average natural season flowering date of Sept. 20.

(8) Average flowering response period of seven (7) weeks in photoperiodic controlled flowering programs.

The accompanying photographic drawings show typical inflorescence and foliage characteristics of Totem. Sheet 1 is a color photograph of Totem. Sheet 2 is a black and white photograph showing three views of the inflorescence of Totem. Sheet 3 is a black and white photograph showing top and bottom leaves of Totem at three stages of growth (mature, intermediate and immature).

Of the many commercially available cultivars known to the present inventor, the most similar existing cultivar in comparison to Totem is Revere, disclosed in U.S. Plant Pat. No. 4,005.

Reference is made to attached Chart A which compares certain characteristics of Totem with the same characteristics of Revere.

It will be noted that in comparison to Revere, Totem has different ray floret color, similar average natural season flower date, and smaller diameter across face of capitulum. The capitulum form, capitulum type, plant height, branching pattern, and plant spread of Totem are similar to those characteristics of Revere.

In the following description, color references are made to The Royal Horticultural Society Colour Chart. The color values were determined between 10:00 and 10:30 A.M. on Sept. 9, 1981 under 150 foot-candle light intensity at Salinas, Calif.

Botanical classification: *Chrysanthemum morifolium*, Ramat., cv Totem.

INFLORESCENCE

Capitulum:

*Form.*—Flat.

*Type.*—Decorative.

*Permanence.*—2 To 3 weeks.

*Diameter across face.*—50 To 60 mm.

Corolla of ray florets:

*Color (abaxial).*—170A Blended with 31A which oxidizes to 23B. The color at center of the flower due to shadowing approximates 171B blended with 34B.

*Color (adaxial).*—170B Streaked with 10A.

Reproductive organs:

*Androecium.*—Present disc florets.

*Gynoecium.*—Present both ray and disc florets.

Disc florets:

*Color.*—14A.

PLANT

General appearance: Spreading branching pattern; medium height.

Foliage:

*Color (abaxial).*—147A.

*Color (adaxial).*—147B.

CHART A

COMPARISON OF TOTEM AND REVERE

| CULTIVAR | RAY FLORET COLOR | CAPITULUM FORM AND TYPE | AVERAGE NATURAL SEASON FLOWER DATE |
|---|---|---|---|
| TOTEM | ORANGE | FLAT | SEPTEMBER 20 |

CHART A-continued

COMPARISON OF TOTEM AND REVERE

| | | | |
|---|---|---|---|
| REVERE | BRONZE BRONZE | DECORATIVE FLAT DECORATIVE | SEPTEMBER 25 |

| CULTIVAR | PLANT HEIGHT | BRANCHING PATTERN AND SPREAD | DIAMETER ACROSS FACE OF CAPITULUM |
|---|---|---|---|
| TOTEM | MEDIUM | SPREADING | 50 to 60 mm. |
| REVERE | SHORT | SPREADING | 55 to 65 mm. |

COMPARISONS MADE OF PLANTS GROWN UNDER NATURAL SEASON OUTDOOR FIELD CONDITIONS IN SALINAS, CALIFORNIA

I claim:

1. A new and distinct cultivar of *Chrysanthemum morifolium*, Ramat., plant known by the name Totem, as described and illustrated, and particularly characterized as to uniqueness by the combined characteristics of flat capitulum form, decorative capitulum type, orange bronze ray floret color, diameter across face of capitulum up to 60 mm., medium plant height, spreading branching pattern, average natural season flowering date of Sept. 20, and average flowering response period of seven (7) weeks in photoperiodic controlled short day programs.

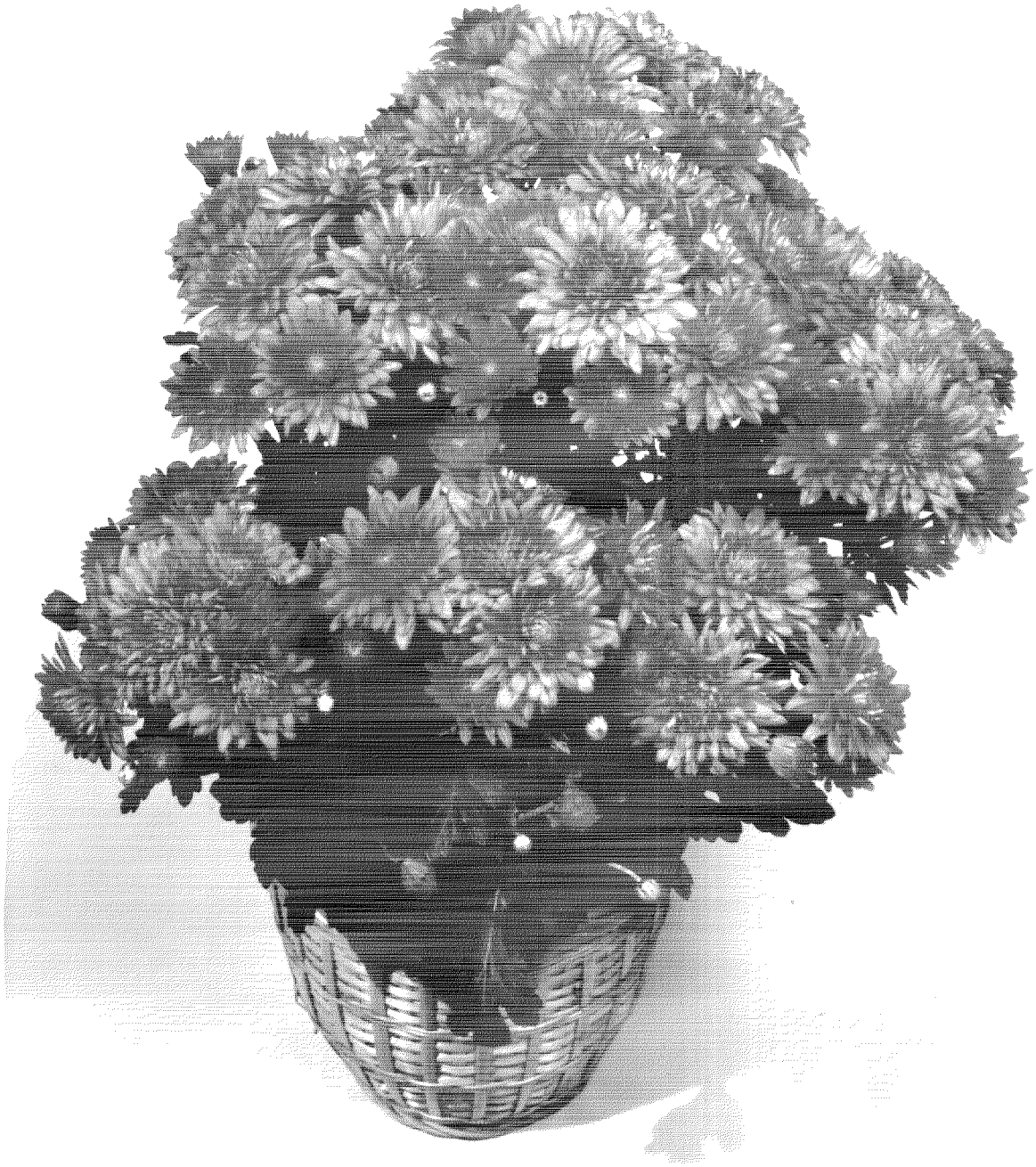

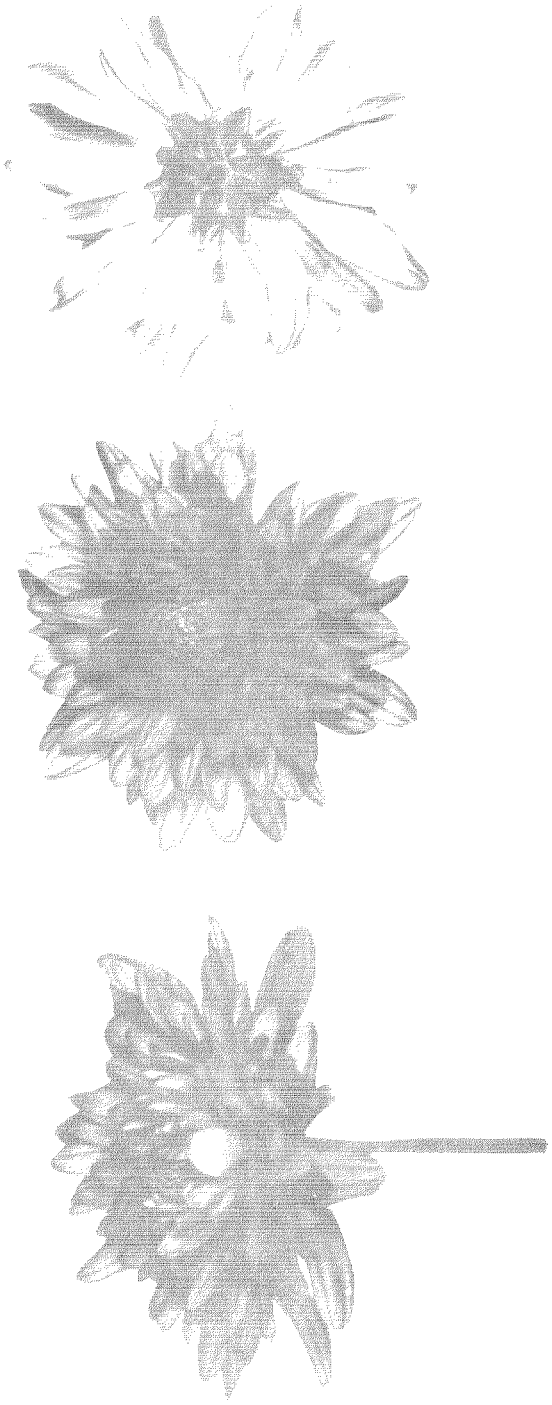

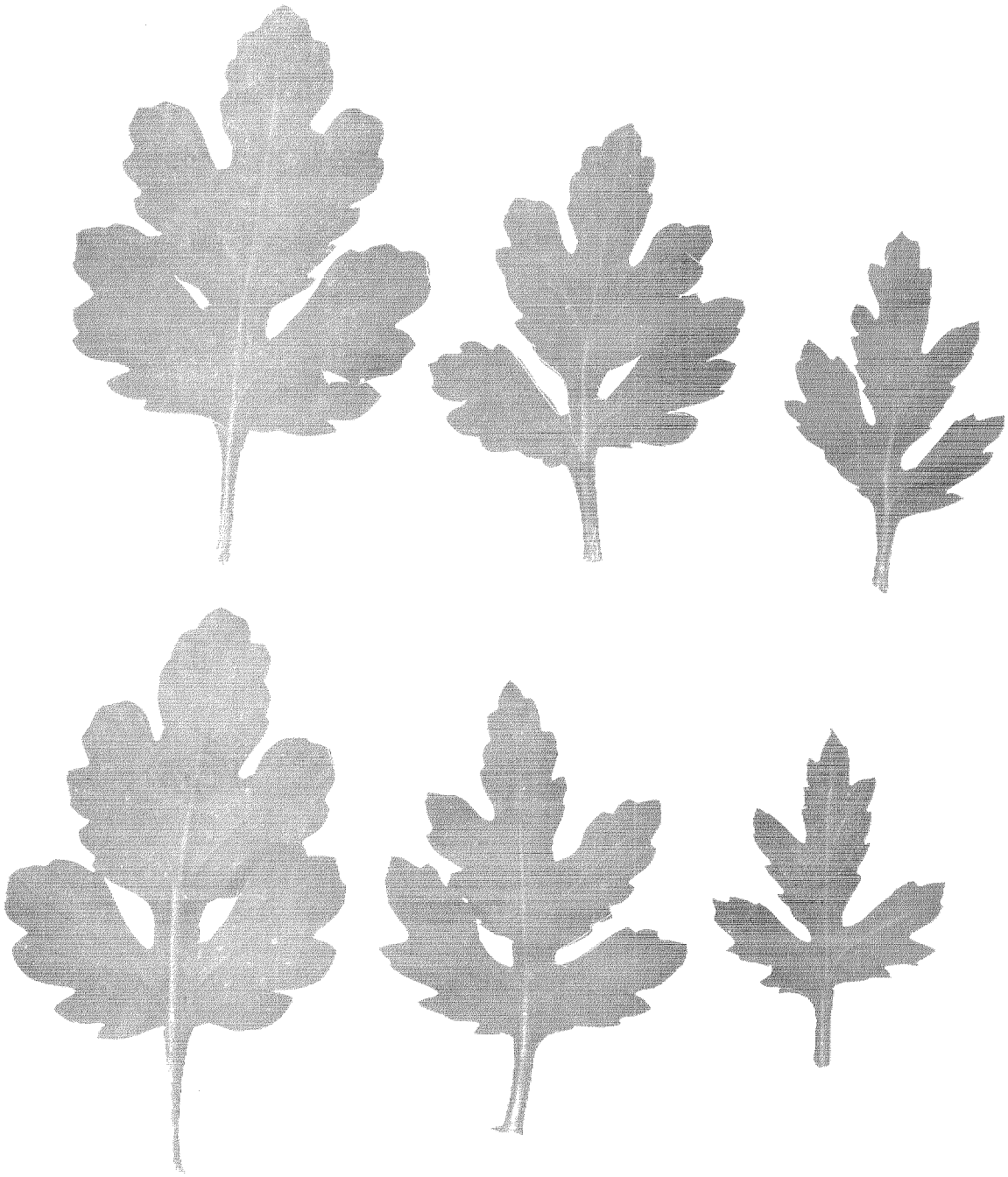

* * * * *